United States Patent [19]

Bloom et al.

[11] Patent Number: 5,141,669

[45] Date of Patent: Aug. 25, 1992

[54] LIQUID CRYSTAL COMPOUNDS HAVING CHIRAL ESTER HEAD GROUPS

[75] Inventors: Iris B. K. Bloom, Quincy; Yunn H. Chiang, Andover; William J. Cumming, Chelmsford, all of Mass.; Russell A. Gaudiana, Merrimack, N.H.; Richard A. Minns, Arlington, Mass.

[73] Assignee: Polaroid Corporation, Cambridge, Mass.

[21] Appl. No.: 373,522

[22] Filed: Jun. 30, 1989

[51] Int. Cl.$^5$ .................. C09K 19/12; C07C 69/76
[52] U.S. Cl. .................. 252/299.65; 560/59; 560/65; 560/73
[58] Field of Search .................. 252/299.01, 299.64, 252/299.65; 560/59, 65, 73

[56] References Cited

U.S. PATENT DOCUMENTS

| | | | |
|---|---|---|---|
| 4,576,732 | 3/1986 | Isogai et al. | 252/299.65 |
| 4,695,650 | 9/1987 | Walba et al. | 560/109 |
| 4,886,619 | 12/1989 | Janulis | 252/299.65 |
| 5,002,693 | 3/1991 | Higashii et al. | 252/299.65 |

FOREIGN PATENT DOCUMENTS

| | | | |
|---|---|---|---|
| 0219958 | 4/1987 | European Pat. Off. | 252/299.64 |
| 8705018 | 8/1987 | World Int. Prop. O. | 252/299.65 |

OTHER PUBLICATIONS

Meyer, R. B., in Mol. Cryst. Liq. Cryst., 40, 33 (1977).
Clark, N. A., et al., in Appl. Phys. Lett. 36, p. 899 (1980).
G. Decobert, et al., in Mol. Cryst. Liq. Cryst., 1984, 114, 237–247.
J. W. Goodby and T. M. Leslie, in "Liquid Crystals and Ordered Fluids", Edited by A. C. Griffin and J. F. Johnson, Plenum Press, vol. 4, pp. 1–32.
J. W. Goodby, in Science, vol. 231, Jan. 24, 1986 pp. 350 and 354.
B. Otterholm, et al., in Liquid Crystals, 1987, vol. 2, No. 6, pp. 757–768.
Chemical Abstracts, 109:219731s, CA Selects: Liquid Crystals, Issue 25, 1988, p. 6.
M. Murakami, et al., in Mol. Cryst. Liq. Cryst., 1988, vol. 162B, pp. 149–156.

*Primary Examiner*—Robert L. Stoll
*Assistant Examiner*—Philip Tucker
*Attorney, Agent, or Firm*—Louis G. Xiarhos

[57] ABSTRACT

Liquid crystal compounds which show a ferroelectric phase and which exhibit high spontaneous polarization values and smectic behavior over a range of temperatures have the formula

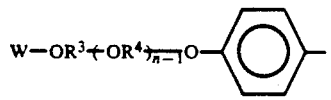

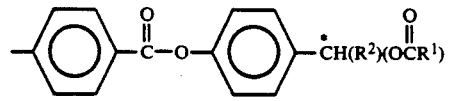

wherein $R^1$ is alkyl of from 1 to 16 carbon atoms; alkoxy; haloalkyl; alkoxyalkyl, wherein the alkoxy substituent thereof comprises a chain of carbon atoms including one or more oxygen ether atoms; or alkoxyalkoxy, wherein the alkoxy substituent thereof comprises a chain of carbon atoms including one or more oxygen ether atoms; $R^2$ is alkyl of from 1 to 4 carbon atoms; each of $R^3$ and $R^4$ is alkylene; n is an integer 1 or 2; and W is alkyl of from 1 to 12 carbon atoms or fluoroalkyl of the formula

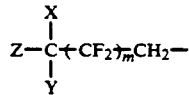

wherein each of X, Y and Z is hydrogen or fluorine, m is zero or an integer from 1 to 6, and at least one of X, Y and Z is fluorine when m is zero.

28 Claims, No Drawings

LIQUID CRYSTAL COMPOUNDS HAVING CHIRAL ESTER HEAD GROUPS

BACKGROUND OF THE INVENTION

This invention relates to certain liquid crystal compounds of the smectic type. More particularly, it relates to smectic liquid crystals which exhibit a ferroelectric, chiral smectic phase and which find application in electrooptic display devices.

The utilization of the properties of a ferroelectric smectic phase to effect a switching phenomenon in an electrooptic display device has been known and is described by N. A. Clark and S. T. Lagerwall in Appl. Phys. Lett. 36, 899 (1980). Such devices operate with low electric power consumption while providing a more rapid switching than is realized in electrooptic display devices dependent upon the properties of liquid crystals of the nematic type. Display devices of the ferroelectric type rely upon two tilted configurations of smectic liquid crystal molecules to provide two states of equal energy. Switching from one state to the other is accomplished by moving a boundary between the two domains by applying an electric field across a pair of electrodes sandwiching a layer of the ferroelectric liquid crystal material.

Examples of ferroelectric liquid crystal compounds of the smectic type are described, for example, by G. Decobert and J. C. Dubois in Mol. Crystl. Liq. Crystl., 1984, 114, 237-247; by J. W. Goodby and T. M. Leslie in "Liquid Crystals and Ordered Fluids", Edited by A. C. Griffin and J. F. Johnson, Plenum Press, Vol. 4, pp. -32; and in U.S. Pat. No. 4,576,732 (issued Mar. 18, 1986 to M. Isogai et al.). Typically, a ferroelectric liquid crystal phase will be a chiral smectic pase such as a chiral smectic C phase ($S_c^*$), a chiral smectic H phase ($S_H^*$), a smectic F phase ($S_F^*$), or a chiral smectic I phase ($S_I^*$). These chiral smectic phaes are characterized in tht the molecules are oriented and form layers. The molecules are aligned aslant in a specified direction on the surface of the layers. The direction of the slope is shifted little by little between the layers so that the phase, as a whole, has a helical structure (R. B. Meyer, Mol. Cryst. Liq. Cryst., 40, 33, 1977).

In the aforeciated U.S. Pat. No. 4,576,732, it is indicated that the appearance of ferroelectricity in a molecular structure is dependent upon two conditions—the presence of an optically active group and the presence of an electric dipole in a direction approximately perpendicular to the major axis of the liquid crystal molecule, to induce spontaneous polarization. In general, it is well recognized that the suitability and operating efficiency of an electrooptic device will be dependent upon the chemical structure of the liquid crystal compound employed therein and that the properties of the liquid crystal compound will be influenced by molecular factors such as rigidity or stiffness, morphology, crystallinity and intermolecular forces.

In the production of ferroelectric liquid crystal compounds of the smectic type for application in a ferroelectric device, it will be a fundamental requirement that the liquid crystal compound (or a liquid crystalline mixture of compounds) exhibit chemical stability. Moreover, it will be highly desirable if the liquid crystal material shows a smectic phase over a wide range of temperatures, particularly, at temperatures in the region of room temperature. In addition, and ideally, the liquid crystal material will exhibit a high level of spontaneous polarization ($P_S$) in order to optimize coupling to an applied electric field. Accordingly, there is considerable interest in chemically stable liquid crystal compounds and compositions which show desirable spontaneous polarization values and smectic behavior over a wide range of temperatures and which can be employed in an electrooptic device for high-speed optical switching, particularly at room temperature.

SUMMARY OF THE INVENTION

The present invention provides a class of chemically stable, smectic liquid crystal compounds which exhibit high spontaneous polarization values and ferroelectric character over a range of temperatures. It has been found that these advantageous properties can be realized by including in the liquid crystal compounds, as a terminal head group thereof, a particular chiral ester moiety, as further described hereinafter. This essential head group is characterized by the presence of an asymmetric carbon atom which is attached directly to an aromatic nucleus of the core segment of the liquid crystal compound and contributes importantly to the ferroelectric character of the liquid crystal material. There is provied, according to the present invention, a class of smectic liquid crystal compounds having the formula (I)

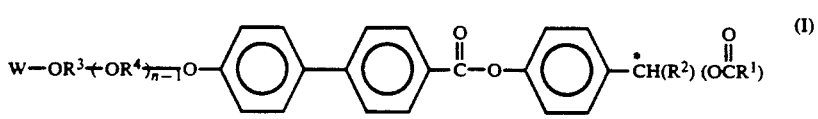

wherein $R^1$ is alkyl of from 1 to 16 carbon atoms; alkoxy; haloalkyl; alkoxyalkyl, wherein the alkoxy substituent thereof comprises a chain of carbon atoms including one or more oxygen ether atoms; or alkoxyalkoxy, wherein the alkoxy substituent thereof comprises a chain of carbon atoms including one or more oxygen ether atoms; $R^2$ is alkyl of from 1 to 4 carbon atoms; each of $R^3$ and $R^4$ is alkylene; n is an integer 1 or 2; and W is alkyl of from 1 to 12 carbon atoms or fluoroalkyl of the formula

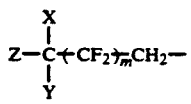

wherein each of X, Y and Z is hydrogen or fluorine, m is zero or an integer from 1 to 6, and at least one of X, Y and Z is fluorine when m is zero.

DESCRIPTION OF THE PREFERRED EMBODIMENTS

The liquid crystal compounds of the present invention will typically show a ferroelectric phase which, as used herein, refers to a smectic phase such as a chiral smectic I phase, a chiral smectic H phase, a chiral smectic F phase or a chiral smectic C phase (which phases are referred to respectively, by the abbreviations $S_I^*$, $S_H{}^*$ and $S_C{}^*$). The smectic liquid crystal compounds of the invention can be used as ferroelectric liquid crystal compounds in a ferroelectric device or can be employed in admixture with other liquid crystal compounds to provide mixtures exhibiting ferroelectric behavior. Preferred liquid crystal compounds of the invention will be those which exhibit the chiral smectic C ($S_c{}^*$) phase especially suited to the provision of compositions useful in ferroelectric display devices.

From inspection of the following structure, representative of the smectic liquid crystal compounds of the invention

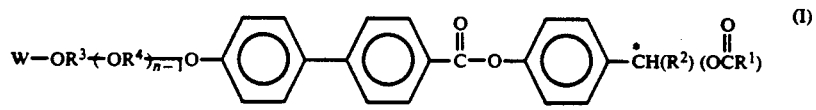

it can be seen that such compounds include a divalent core segment of the formula (Ia)

(Ia)

and terminal moieties (Ib) and (Ic), which for convenience are referred to, respectively, as "head" and "tail" moieties and which have the respective formulas $$-\overset{*}{C}H(R^2)(O\overset{O}{\underset{\|}{C}}R^1) \quad (Ib)$$

and $$W-OR^3 (OR^4)_{\overline{n-1}} O- \quad (Ic)$$

The respective head and tail groups especially, and the core segment to which they are attached, relate importantly to particular properties observed in the smectic liquid crystal compounds of the invention. Accordingly, such groups and the manner in which they are incorporated into the smectic liquid crystal compounds of the invention are described in detail hereinafter.

The liquid crystal compounds of the invention are from amoung the ester class, having an ester linkage between the aromatic radicals of the core segment. These ester compounds can, thus, be prepared by using a method which, for example, includes the following steps:

a first esterification step, involving the reaction of a biphenyl carboxylic compound with an enantiomerically enriched phenol compound which has an hydroxyl group attached to the chiral atom thereof; and a second esterification step, for converstion of the hydroxyl group on the chiral atom to an ester group. This combination of steps is illustrated by the following sequence of reactions:

Esterification Reaction Scheme A:

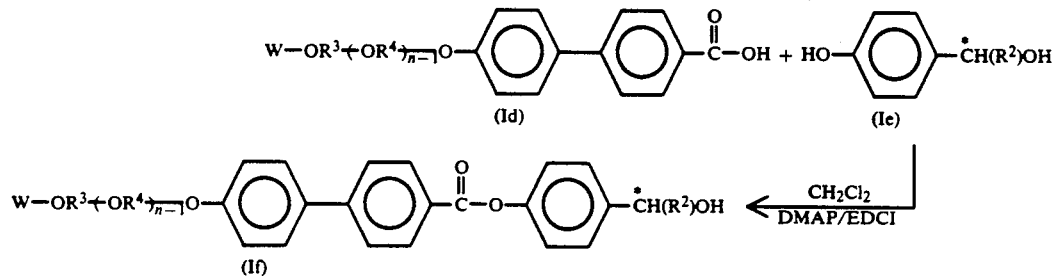

Esterification Reaction Scheme B:

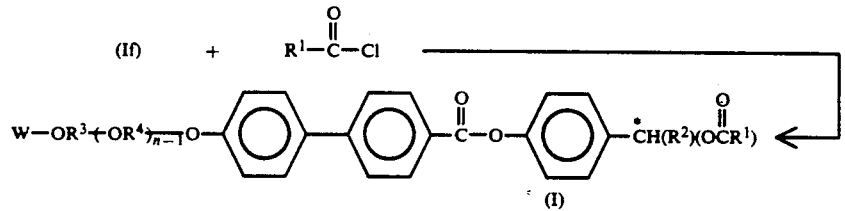

In general, the esterification reaction represented by Esterification Reaction Scheme A can be conducted in a suitable organic solvent such as methylene chloride, using known activator or catalyst compounds such as 4-dimethylaminopyridine (DMAP) and 1-(3-dimethylaminopropyl-3-ethylcarbodiimide (EDCI). The esterification can be conducted at room temperature and according to known esterification methods.

As shown in Esterification Reaction Scheme A, the formula-(If) intermediate compound contains an hydroxy group on the chiral carbon atom. This hydroxyl group is converted to an ester group by the second esterification reaction, shown as Esterification Reaction Scheme B, using, for example, an acyl chloride of the formula

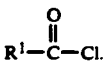

This second esterification can be performed in an organic solvent such as methylene chloride, using a trialkylamine such as triethylamine as an acid acceptor. Other esterification techniques can, however, be used; and suitable methods involve those based upon the diacid anhydride reactant in place of the acid chloride. The corresponding acid can also be used to conduct the desired esterification. For example, the formula-(If) intermediate can be reacted with a carboxylic acid such as 2-methylbutyric acid, in which case, the $R^1$ group is 2-butyl. It will be appreciated that where a carboxylic acid compound is used for esterification of the formula(If) intermediate, suitable activators or catalysts should be utilized. Suitable materials for this purpose are those mentioned previously in connection with the conduct of the reaction of Esterification Reaction Scheme A.

The ferroelectric properties of the liquid crystal compounds of the invention, and particularly the spontaneous polarization values, will be materially influenced by the head group. It is an important structural feature of the liquid crystal compounds of the invention that the chiral carbon atom of the formula-(Ib) head group is attached directly to the phenylene radical of the formula-(Ia) core segment. While the applicants do not wish to be bound by any particular theory in explanation of the high values of spontaneous polarization obtained for the liquid crystal compounds of the invention, the proximity of the chiral carbon atom of the head group to the core segment is believed at least in part to contribute to such high values.

The $-R^2$ substituent of the head group and the

group attached to the chiral atom can vary in position with respect to each other, so as to form optical isomers. Thus, the liquid crystal compounds of the invention can be used in either the (R) or (S) isomeric forms, or in admixture.

The $R^2$ group is an alkyl group having from 1 to 4 carbon atoms. Suitable examples include methyl, ethyl and n-butyl. Good results are obtained in the case of liquid crystal compounds wherein $R^2$ is methyl. In addition, from the standpoint of ease of preparation, compounds of the invention wherein $R^2$ is methyl will be preferred.

Suitable $R^1$ groups include alkyl of from 1 to 16 carbon atoms. Such alkyl groups include methyl, ethyl, n-propyl, n-butyl, n-hexyl, n-heptyl, n-octyl, n-undecyl n-dodecyl and n-hexadecyl. If desired, the $R^1$ alkyl group can be branched and suitable examples include isopropyl, isobutyl, the 2-methyl-1-butyl group, the 2-butyl group, and the 2-heptyl and 2-octyl groups. A preferred branched alkyl group is the 2-methyl-1-butyl group.

$R^1$ can also be a haloalkyl group inclusive of alkyl groups having one or more halogen (e.g., chlorine or fluorine) atoms. Suitable examples include chloromethyl, trifluoromethyl, 2-chloro-1-propyl, 2-fluoro-1-propyl, 1-chloroethyl and 1-fluoroethyl. Preferred haloalkyl groups contain from 1 to 3 carbon atoms and from 1 to 3 halogen atoms, such as are represented by 1-chloroethyl and trifluoromethyl.

If desired, $R^1$ can be alkoxy which, in general, will have from 1 to 6 carbon atoms, inclusive of such alkoxy groups as ethoxy and 2-butoxy.

In addition to alkyl as mentioned hereinbefore, $R^1$ can be alkoxyalkyl, the alkoxy substituent being a single alkoxy group attached to the alkyl, or a multiple alkoxy group attached to the alkyl, such as an alkoxyalkoxyalkyl group. The chain of carbon atoms of the alkoxy substituent can, thus, include one or more, usually 1 to 3, oxygen ether atoms. Suitable alkoxyalkyl $R^1$ groups include those represented by the formulas $-R^5-OR^6$; $-R^5-OR^7-OR^8$; and $-R^5-OR^7-OR^9-OR^{10}$; wherein $R^5$, $R^7$, and $R^9$ are alkylene and $R^6$, $R^8$ and $R^{10}$ are alkyl Examples of suitable alkoxyalkyl groups include ethoxymethyl; 2-methoxyethyl; 2-butoxyethyl; 2,5-dioxaheptyl; 3,6-dioxaoctyl; and 3,5,7-trioxanonyl. A preferred alkoxyalkyl group is 2-ethoxyethyl.

Similarly, $R^1$ can be alkoxyalkoxy, the alkoxy substituent group thereof comprising a chain of carbon atoms including one or more, typically 1 or 2, carbon atoms. Suitable alkoxyalkoxy groups are those represented by the formulas $-OR^5-OR^6$; $-OR^5-OR^7-OR^8$; and $-OR^5-OR^7-OR^9-OR^{10}$; wherein $R^5$, $R^7$ and $R^9$ are alkylene and $R^6$, $R^8$ and $R^{10}$ are alkyl. Examples of suitable alkoxyalkoxy groups include 2-methoxyethoxy; 2-butoxyethoxy; and 2-[2-(ethoxy)ethoxy]ethoxy.

The $R^1$ group attached to the chiral atom of the formula-(Ib) head group can vary as aforedescribed and can itself contain a chiral atom. Suitable examples of chiral $R^1$ groups include 2-butyl; 2-butoxy; 1-chloroethyl; and 1-fluoroethyl.

The $R^1$ group will be introduced into the formula-(I) liquid crystal compounds of the invention via the esterification reaction previously described. Suitable representative acyl halides for this purpose include propionyl chloride; heptanoyl chloride; octanoyl chloride and dodecanoyl chloride. Suitable carboxylic acid reactants include (R)-(+)-2-chloropropionic acid; (S)-(−)-2-chloropropionic acid; (S)-2-methylbutyric acid and 3-ethoxypropionic acid. Corresponding diacid anhydrides can also be used, if desired.

The intermediate compound of formula (Ie) in Esterification Reaction Scheme A supplies the precursor group of the chiral head grop of the compounds of the invention and can be prepared by the enantioselective reduction of the keto group of a blocked phenol compound using, for example, (+)-β-chlorodiisopinocampheylborane (or the (−)-β-chlorodiisopinocampheylborane enantiomer); and by a hydrolytic deblocking reaction for production of the desired intermediate compound of formula (Ie). This is illustrated in the following sequence of reactions, wherein BG represents a hydrogen blocking group such as benzoyl, i.e., $C_6H_5C(O)-$.

Reduction Reaction Scheme:

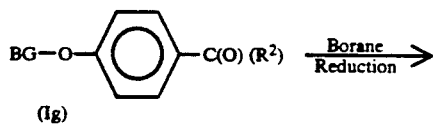

(Ig)

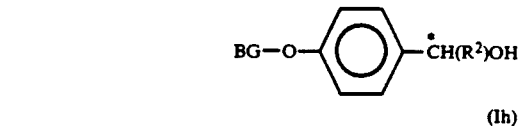

(Ih)

Deblocking Reaction Scheme:

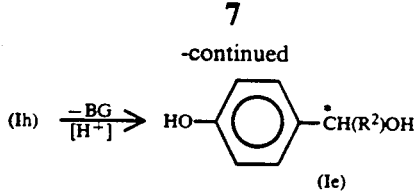

The formula-(Ic) tail group of the liquid crystal compounds of the invention is a moiety which contains oxygen ether atoms, and optionally, fluorine atoms. The formula-(Ic) tail moiety contributes importantly to the breadth of the range of temperatures over which smectic behavior may be observed. In the tail group of the formula

each of $R^3$ and $R^4$ represents a divalent alkylene radical, for example, having from 1 to 6 carbon atoms (e.g., methylene; 1,2-ethylene; 1,3-propylene; 1,4-butylene and hexamethylene). Preferably, each of $R^3$ and $R^4$ will be the same and will be 1,2-ethylene.

Subscript n is an integer of 1 or 2 and, thus, the tail moiety will be a diether (n=1) or a triether (n=2). Preferably, n will be 2.

In the oxygen ether-containing tail moiety of formula (Ic), W can be an alkyl group which can be branched or straight chained. Typically, alkyl group W, will have from 1 to 12 carbon atoms (e.g., methyl, ethyl, butyl, hexyl, decyl or dodecyl). Preferably, alkyl group W will have from 1 to 4 carbon atoms, and especially 2 or 4 carbon atoms (e.g., ethyl or n-butyl).

Among preferred formula-(Ic) tail groups are those represented by the following formulas $$W-OR^3-O-\quad\text{(Ic-1)}$$

wherein W is alkyl of from 1 to 4 carbon atoms, preferably 2 or 4 carbon atoms, and $R^3$ is alkylene having 1 or 2 carbon atoms, preferably, 1,2-ethylene;

$$W-OR^3-OR^4-O-\quad\text{(Ic-2)}$$

wherein W is alkyl of from 1 to 4 carbon atoms, preferably 2 or 4 carbon atoms, $R^3$ and $R^4$ each have from 1 to 4 carbon atoms, and especially are each 1,2-ethylene.

Examples of these preferred tail moieties include those represented by the following formulas:

$$C_4H_9-O-C_2H_4-O-\quad\text{(Ic-1a)}$$

$$C_2H_5-O-C_2H_4{}_{6l}-O-C_2H_4-O-\quad\text{(Ic-2a)}$$

$$C_4H_9-O-C_2H_4-O-C_2H_4-O-\quad\text{(Ic-2b)}$$

Suitable tail groups can be incorporated into liquid crystal compounds of the invention by using a formula-(Id) intermediate, as shown in ester Reaction Scheme A, having the predetermined and desired tail moiety. The synthesis of formula-(Id) intermediates can be accomplished by the alkylation of an alkyl 4-hydroxybiphenyl-4'-carboxylate, using an oxygen ether-containing alkyl halide, such as the bromide; and alkaline hydrolysis of the ester to the corresponding acid, as illustrated in the following sequence of reactions, wherein $R^{11}$ is alkyl (e.g., methyl):

Alkylation Reaction Scheme:

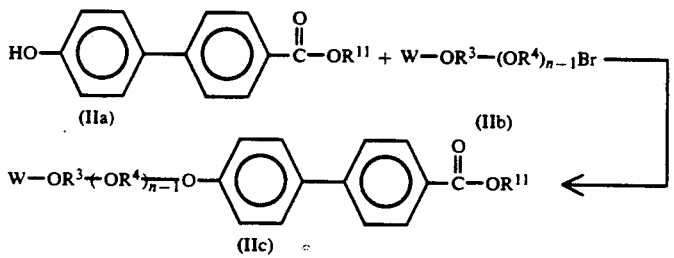

Hydrolysis Reaction Scheme:

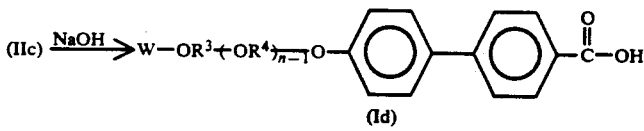

The terminal group W of the tail moiety can also be a fluoroalkyl group having the formula

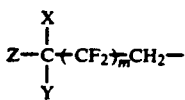

wherein each of X, Y and Z is hydrogen or fluorine, m is zero or an integer from 1 to 6, and at least one of X, Y and Z is fluorine when m is zero.

Each of X, Y and Z can independently be hydrogen or fluorine. In one preferred tail group, each of X and Y is fluorine and Z is hydrogen In another preferred group, each of X, Y and Z is fluorine, i.e., trifluoromethyl. When m is not zero, it will be an integer of from 1 to 6. Preferably, m is an integer of from 2 to 5.

Other preferred formula-(Ic) tail groups are those oxygen ether-containing tail groups containing fluorine atoms, as represented by the following formulas:

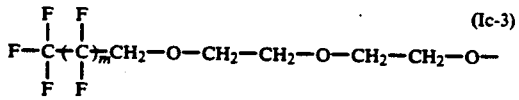

wherein m is from 1 to 5, and preferably, 3;

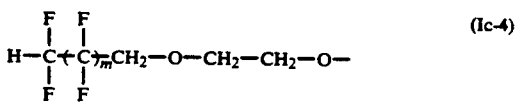

wherein m is from 1 to 5, and preferably, 3; and

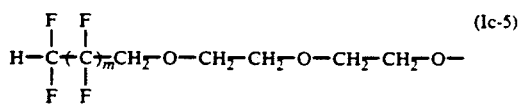

wherein m is from 1 to 5, and preferably, 3.

The preferred formula(Ic-3), -(Ic-4) and -(Ic-5) tail groups can be incorporated into liquid crystal compounds of the invention by using a formula-(Id) intermediate, as shown in Ester Reaction Scheme A, having the predetermined and desired tail moiety. A suitable formula-(Id) intermediate which embodies a formula-(Ic-4) type of tail moiety is the compound of the following formula

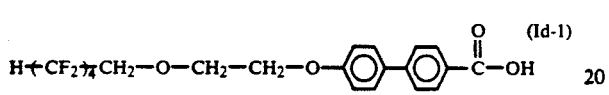

This intermediate can be prepared from 1H, 1H, 5H-octafluoro-1-pentanol by a series of steps including salt formation (Step 1); reaction with ethyl bromoacetate (Step 2); lithium aluminum hydride reduction (Step 3); sulfonate ester formation, using p-toluenesulfonyl chloride (Step 4); etherification, by reaction with methyl 4'-hydroxy-4-biphenylene carboxylate (Step 5); and hydrolysis/acidification, to provide the formula-(Id-1) intermediate (Step 6):

Step 1:

Step 2:

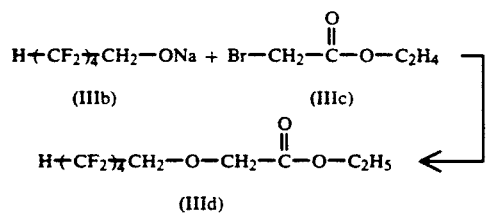

Step 3:

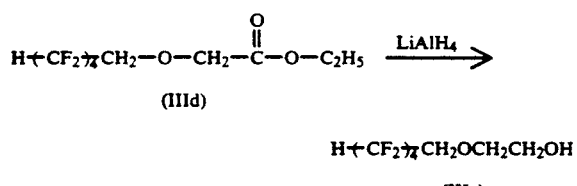

Step 4:

H₂(CF₂)ₙCH₂—O—CH₂—CH₂—OH $\xrightarrow{\text{p-toluenesulfonyl chloride}}$ (IIIe)

-continued

H₂(CF₂)ₙCH₂—O—CH₂—CH₂—O—S(O)₂—⌬—CH₃

(IIIf)

Step 5:

H₂(CF₂)ₙCH₂OCH₂CH₂OS(O)₂—⌬—CH₃ +

(IIIf)

HO—⌬—⌬—C(O)—OCH₃ →

(IIIg)

H₂(CF₂)ₙCH₂—O—CH₂—CH₂—O—⌬—⌬—C(O)—OCH₃

(IIIh)

Step 6:

H₂(CF₂)ₙCH₂—O—CH₂—CH₂—O—⌬—⌬—C(O)—OCH₃ $\xrightarrow[\text{2) H}^+]{\text{1) OH}^-}$ (IIIh)

H₂(CF₂)ₙCH₂—O—CH₂—CH₂—O—⌬—⌬—C(O)—OH (Id-1)

The formula-(I) liquid crystal compounds of the invention include those having a triether tail moiety. A preferred triether tail containing fluorine atoms, such as is represented by the formula-(Ic-5) tail group, can be prepared by suitable modifications of the described route to the formula-(Id-1) intermediate. Thus, in the illustrated preparative route, the compound of formula (IIIe) can be reacted with sodium hydride for conversion to the corresponding alcoholate salt. Reaction of the salt with ethylene oxide, followed by acidification provides the compound (IVa)

H₂(CF₂)ₙCH₂—O—CH₂—CH₂—O—CH₂—CH₂—OH
2—OH     (IVa)

which can be reacted in a series of steps analogous to Steps 4 to 6, to provide the intermediate compound of the formula (Id-2)

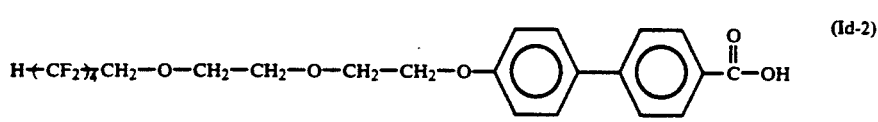

Liquid crystal compounds of the ferroelectric type having oxygen ether-containing tail moieties are disclosed and claimed in the copending application of W. J. Cumming, et al., U.S. Ser. No. 061,072, filed June 23, 1987. Liquid crystal compounds of the ferroelectric type having oxygen ether and fluorine atoms in the tail moieties thereof are disclosed and claimed in the co-pending application of Y. H. Chiang et al., U.S. Ser. No. 255,477, filed Oct. 11, 1988. Intermediates containing these tail moieties and described in the aforecited patent application Ser. Nos. 061,072 and 255,477 can be used as intermediates in the production of liquid crystal compounds of the present invention and methods disclosed therein for the synthesis of such intermediates can be used to advantage.

Among the liquid crystal compounds of the invention are the following compounds.

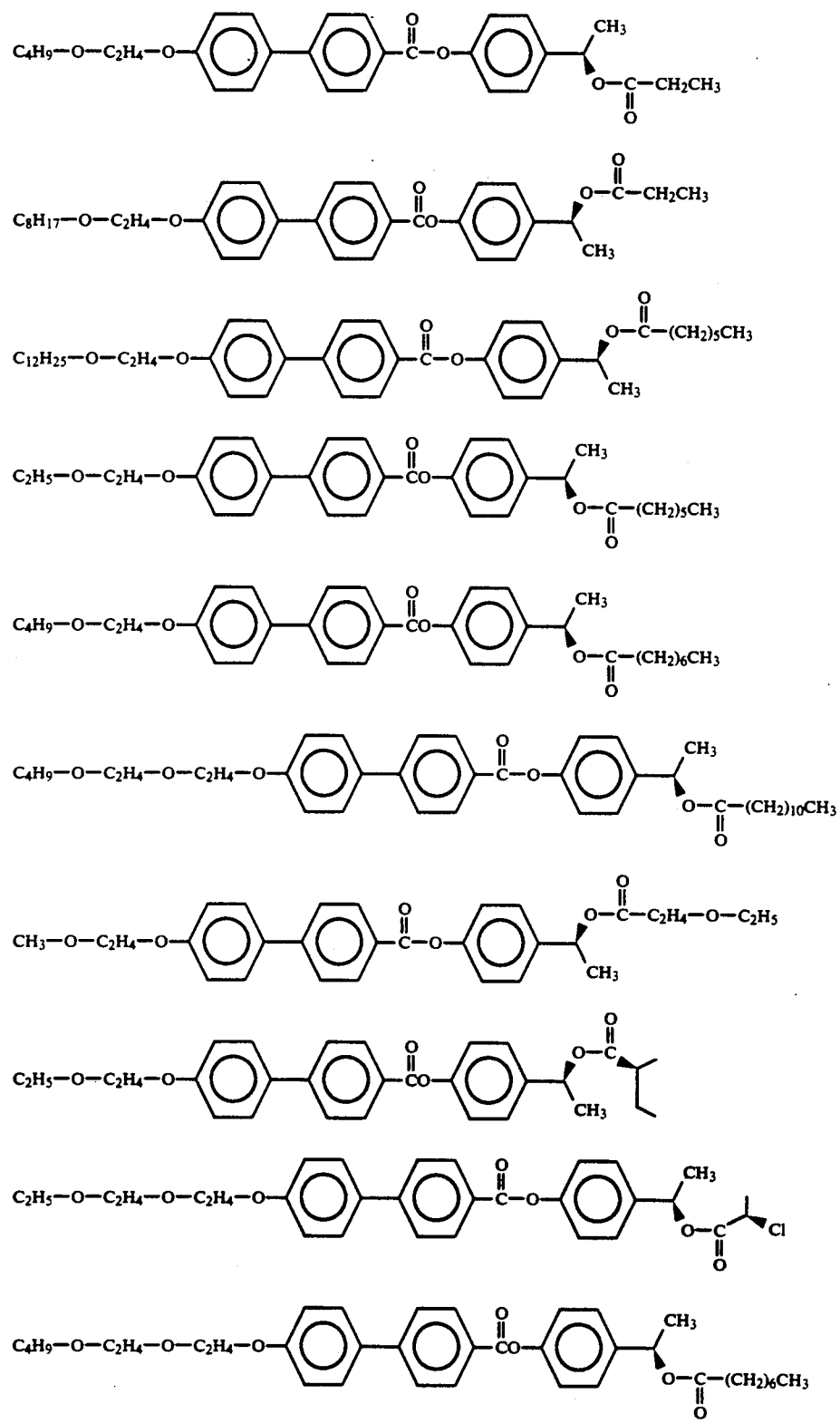

-continued
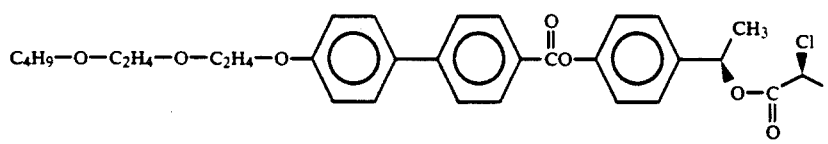
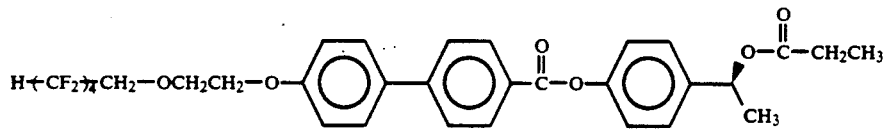
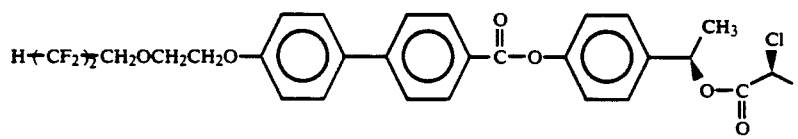
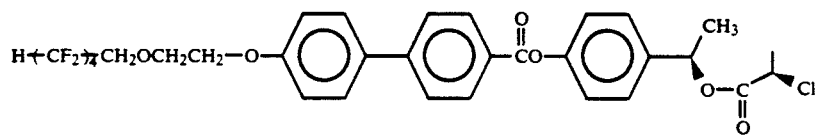
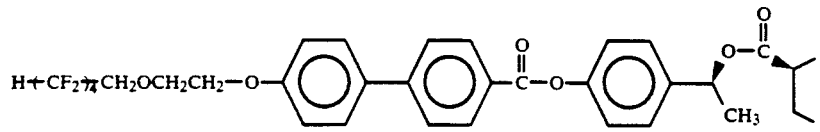
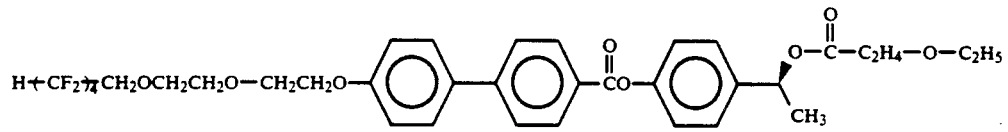
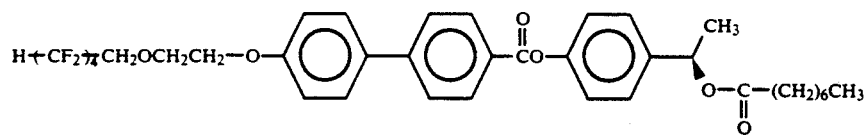
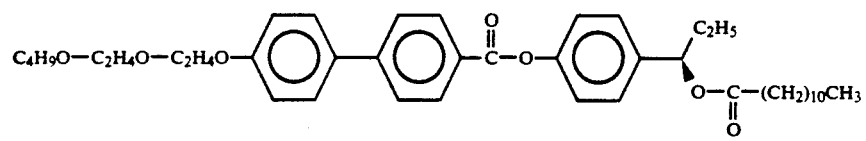
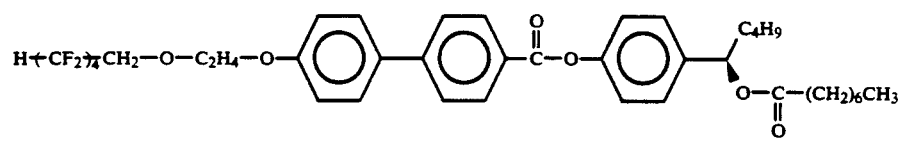
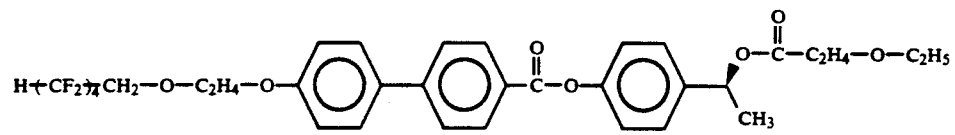
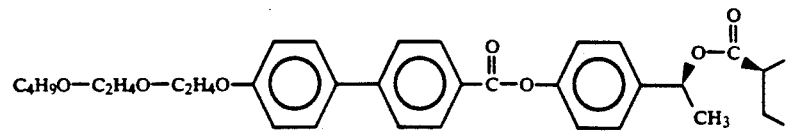

-continued

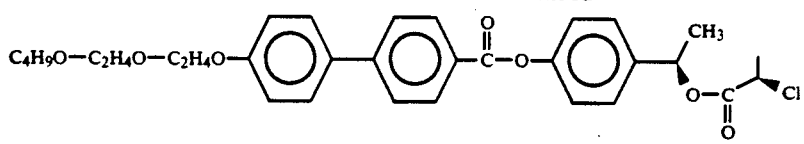

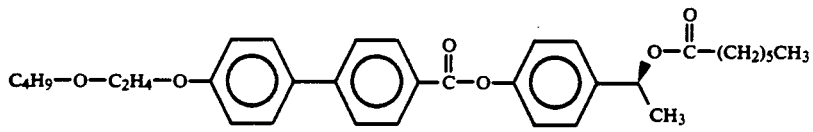

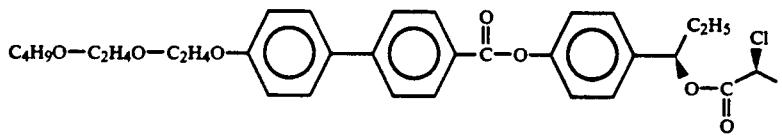

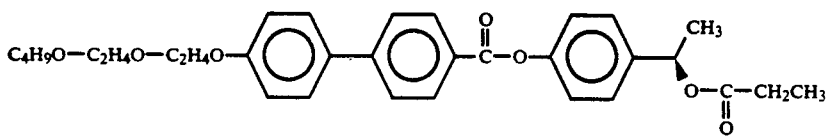

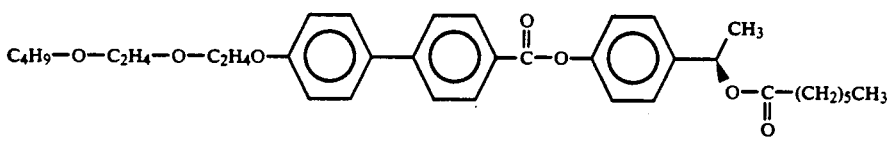

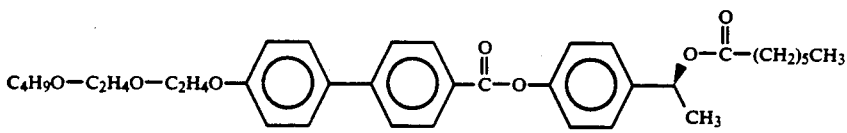

Structural variations within the class of liquid crystal compounds represented by formula (I) will produce corresponding variations in observed phase transitions, spontaneous polarization, orientational viscosity and other properties of interest in connection with ferroelectric liquid crystal materials intended for application in electrooptic devices. In general, however, the liquid crystal compounds of the invention exhibit a desired combination of high spontaneous polarization and smectic behavior over a wide range of temperatures, and particularly, over a range of room temperatures. As a consequence, the liquid crystal compounds of the invention are suited to application in an electrooptic device for high-speed optical switching, especially at room temperature. The liquid crystal compounds of the invention exhibit rapid switching in a display device comprising a liquid crystal compound of the invention confined, as is known in the art, between a pair of plates having electrodes thereon and means for providing a voltage across the electrodes.

The liquid crystal compounds of the invention can be used alone or in admixture with other liquid crystal compounds which may or may not exhibit a smectic mesophase. It is a particular advantage of the liquid crystal compounds of the invention that certain of the compounds exhibit a sufficiently wide temperature range of smectic behavior as not to require the use of the compounds in admixture with other compounds. As is known in the art, mixtures of liquid crystalline compounds are oftentimes formulated with the objective of broadening the range over which a smectic mesophase is observed Typically, an admixture of compounds is formulated to identify an optimal or eutectic composition. Good results can, however, be obtained—owing to the breadth of the range of temperatures over which smectic behavior is exhibited—using a single compound. In this connection, and for purposes of illustration, the compound of the invention, (S)-4-[1-(3-ethoxypropionyloxy)ethyl]phenyl 4-[2-(1H, 1H, 5H-octafluoro-1-pentoxy)ethoxy]biphenyl-4'-carboxylate shows a smectic C range on heating from the crystalline phase of 52° C. (8° to 60° C.), measured by differential scanning calorimetry.

The compounds of the invention can, if desired, be used in admixture with a variety of liquid crystalline compounds. A compound of formula (I) can be used in combination with one or more compounds also within the class represented by formula (I), or in admixture with one or more other compounds which may or may not exhibit ferroelectric or other liquid crystalline behavior but which may be employed to alter the freezing, melting or other behavior of the resulting ferroelectric composition.

The following non-limiting examples are illustrative of the practice of the present invention.

EXAMPLE 1

This example illustrates the preparation of (R)-4-(1-propionyloxyethyl)phenyl 4-[2-(2-butoxyethoxy)ethoxy]biphenyl-4'-carboxylate.

Part A—Preparation of 4-benzoyloxyacetophenone. Into a 500 ml, three-necked, round-bottom flask equipped with a magnetic stirrer, a thermometer, and an addition funnel were added 13.6 g (0.10 mole) 4-hydroxyacetophenone and 15 ml (0.108 mole) triethylamine dissolved in 200 ml of methylene chloride. The resulting solution was maintained under a nitrogen atmosphere and cooled to 5° C. in an ice-water bath. With stirring, a solution of 12 ml (0.103 mole) benzoyl chloride in 40 ml of methylene chloride was added dropwise over 30 minutes; then, the mixture was allowed to stand overnight at room temperature. The mixture was extracted first with dilute aqueous hydrochloric acid, then with water, and finally with a half-saturated sodium bicarbonate solution. The organic phase was dried and evaporated on a rotary evaporator. The product was recrystallized from methylene chloride/hexanes to yield 20.3 g (84%) of cream-colored crystals having a melting point of 138°-140° C. The following structure was confirmed by mass spectral analysis

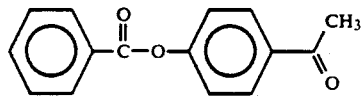

Part B—Preparation of (R)-4-(1-hydroxyethyl)phenyl benzoate. Into a 250 ml, three necked, round-bottom flask equipped with a magnetic stirrer, a thermometer, and an addition funnel were added 5.0 g (20.8 mmole) 4-benzoyloxyacetophenone (prepared as described in Part A of this Example) and 80 ml anhydrous tetrahydrofuran (THF). The resulting solution was maintained under nitrogen and cooled to 2° C. in an ice-water bath. With stirring, 25 ml (25.0 mmole) of a 1.0 molar solution of (+)-β-chlorodiisopinocampheylborane in methylene chloride was added dropwise over 45 minutes. A white precipitate, which formed during the addition, dissolved soon after the addition was finished. After the solution was then stored in a refrigerator (5° C.) for four days, it was added to 100 ml of methanol and evaporated. Addition of 100 ml of pentane yielded a white precipitate which was comminuted, filtered, washed with pentane, and dried to yield 4.90 g of crude product. This product was purified by flash chromatography through a 7×17 cm silica gel column with 5% ethyl ether/methylene chloride as eluant. The chromatographically purified product was recrystallized from methylene chloride/cyclohexane to yield 4.30 g (85%), m.p. 122°-3° C., $[\alpha]_D^{25} = +28.6°$ (c=10, THF), of desired product having the following structure, confirmed by NMR and mass spectral analyses The enantiometric excess (nearly 100%) was determined by the $^{31}$P NMR method of Feringa, et al. J. Am. Chem. Soc., 107, 4798 (1985).

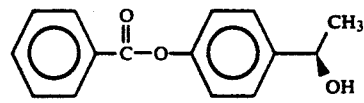

Part C—Preparation of (R)-4-(1-hydroxyethyl)phenol. A solution of 4.0 g (16.5 mmole) of (R)-4-(1-hydroxyethyl)phenyl benzoate (prepared as described in Part B of this Example), 25 ml of tetrahydrofuran, 30 ml of methanol, and 13.2 ml (33 mmol) of 10% aqueous sodium hydroxide was stirred for 30 minutes at room temperature and then evaporated on a rotary evaporator with the bath at 35° C. until most of the methanol and tetrahydrofuran was removed. The resulting solution was acidified with 8 ml of 10% aqueous hydrochloric acid and then buffered to pH 8 by adding 50 ml of saturated aqueous sodium bicarbonate solution. This solution was extracted five times with 50 ml of ethyl ether, and the combined organic phase was dried and distilled. Toluene (150 ml) was added and the distillation was continued to remove ether, methanol, tetrahydrofuran, and water as the vapor temperature rose to the boiling point of toluene (110° C.). When crystals began to form, the mixture was cooled to 0° C. and filtered. The white crystals were washed with pentane and dried to yield 2.14 g (94%), m.p. 150°-3° C., $[\alpha]_D^{25} = 53.0$ (c=10, THF), of desired product having the following structure, confirmed by NMR and mass spectral analyses.

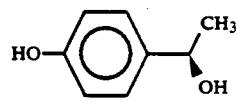

Part D—Preparation of methyl 4-[2-(2-butoxyethoxy)ethoxy]biphenyl-4'-carboxylate. A mixture of 3.4 g (15 mmol) of methyl 4-hydroxybiphenyl-4'-carboxylate, 3.6 g (160 mmol) of 1-bromo-3,6-dioxadecane, 4.2 g of powdered potassium carbonate, and 300 mg of potassium iodide were heated in 35 ml of dimethylformamide for four hours at a temperature of 125° to 130° C. The reaction mixture was poured slowly into 250 ml of ice water and was stirred for one-half hour. The resulting precipitate was collected by filtration, washed with water and dried in a vacuum oven at 40° C. overnight, yielding 5.3 g of crude product. The crude product (2.9 g) was extracted three times with 100 ml of boiling hexane and the combined hexane solution was evaporated to a total volume of about 80 ml. A colorless solid (m.p. 90°-92° C.), weighing 2.1 g (72% yield) after standing for 5 hours at room temperature, was obtained. The mother liquor was concentrated to a volume of about 30 ml to provide an additional quantity of product in the amount of 0.26 g (9% yield). This portion, also a colorless solid, had a melting point of 91°-93° C. The following structure of the desired product was confirmed by IR, NMR, and mass spectral analyses.

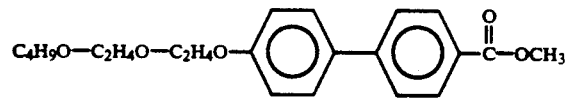

Part E—Preparation of 4-[2-(2-butoxyethoxy)ethoxy]biphenyl-4'-carboxylic acid. A mixture of two grams (5.4 mmol) of the ester product prepared as described in Part D of this Example, two ml of 50% aqueous sodium hydroxide, 30 ml of methanol and 10 ml of water was heated on a steam bath. A homogeneous solution was obtained. A colorless solid was observed to precipitate from the solution as methanol was removed by heating. Fifty ml of water were added and the suspension was left on the steam bath for two hours. The reaction mixture was diluted with water to a total volume of 300 ml, acidified with concentrated hydrochloric acid, heated to a boil, and cooled in an ice-water-salt bath. The colorless precipitate was collected by filtration, washed with water and dried in a vacuum oven at 60° C. overnight, to provide 1.87 g (97% yield) of a product having a melting point of 174°-176° C. and the following structure.

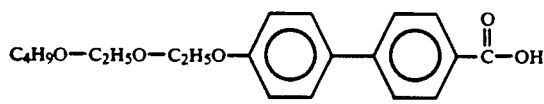

Part F—Preparation of (R)-4-(1-hydroxyethyl)phenyl 4-[2-(2-(butoxyethoxyethoxyl-biphenyl-4'-carboxylate. A mixture of 250 mg (1.809 mmol) of (R)-4-(1-hydroxyethyl)phenol from Part C of this Example, 714.0 mg (1.1 eq.) of 4-[2-(2-butoxyethoxy)ethoxy]-biphenyl-4'-carboxylic acid from Part E, 521.3 mg (1.5 eq.) of 1-(3-dimethylaminopropyl)-3-ethyl carbodiimide hydrochloride [EDCI] and 110.7 mg (0.5 eq.) of 4-dimethylaminopyridine in 25 ml dry methylene chloride was stirred overnight under nitrogen at room temperature. The solvent was removed and the residue was passed through a silica gel flash chromatography column using 5% ethyl ether/ methylene chloride as eluant to afford 471.0 mg (54.4% yield) of the desired ester having the following formula, confirmed by proton NMR spectral analysis.

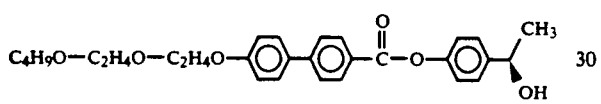

Part G—Preparation of (R)-4-(1-propionyloxyethyl)-phenyl 4-[2-(2-butoxyethoxy)-ethoxylbiphenyl-4'-carboxylate. A mixture of 100 mg (0.209 mmol) of (R)-4-(1-hydroxyethyl)phenyl 4-[2-(2-butoxyethoxy)ethoxyl-biphenyl-4'-carboxylate from Part F of this Example and triethylamine (1.3 eq.) in 3 ml dry methylene chloride was stirred at room temperature under nitrogen. The solution was cooled in an ice-water bath to 5° C. A solution of 1.1 eq. of propionyl chloride in 0.5 ml methylene chloride was added to the reaction via syringe and stirred overnight while warming to room temperature. The reaction was quenched with dilute hydrochloric acid. The organic phase was transferred to a separatory funnel and was washed with water, saturated aqueous sodium bicarbonate solution, and water, and then dried over anhydrous sodium sulfate. The solvent was evaporated. The product was purified on a preparative chromatography plate (20×20 cm) using 6% ethyl ether/methylene chloride as the developing solvent to yield 31.9 mg (28%) of the desired ester having the following structure, confirmed by NMR spectral analysis.

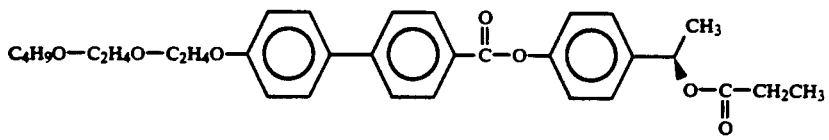

Phase transition temperatures for the compound of this Example were determined using differential scanning calorimetry (DSC) and microscopic evaluation. The temperatures at which the phase transitions occurred were determined by heating and cooling techniques, for the provision of data for the production of heating and cooling curves, respectively Cooling data were obtained by first heating the compound sufficiently to assure that the compound was in an isotropic state, and then, cooling gradually (usually at 10° C./min) and recording the temperature for each phase transition. Heating data were obtained by first cooling the compound to a crystalline state, and then, heating gradually (usually at 10° C./min) and recording the temperature for each phase transition. Phase transitions reported herein are in degrees Centigrade (°C). "I" refers to isotropic; "$S_A$" refers to smectic A; "$S_C$" refers to smectic C; "K" and "K'" refer, respectively, to different crystalline phases; and "J/g" refers to Joules per gram.

The following data were obtained for the compound of EXAMPLE 1.

Microscopy data:

DSC data:

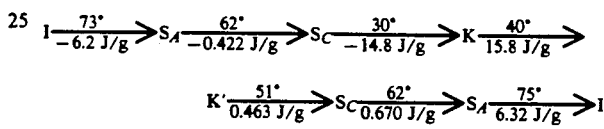

EXAMPLE 2

This example illustrates the preparation of (S)-4-(1-propionyloxyethyl)phenyl 4-[2-(2-butoxyethoxy)ethoxy]biphenyl-4'-carboxylate.

Part A—Preparation of (S)-4-(1-hydroxyethyl)phenyl benzoate. Using the procedure described in EXAMPLE 1, Part B, and using (−)-β-chlorodiisopinocampheylborane in lieu of (+)-β-chlorodiisopinocampheylborane, an enantiomer having the same melting point of 122°-3° C. as the (R)-isomer, but having the opposite optical rotation $[\alpha]_D^{25} = -28.6°$ (c=10 THF), was prepared:

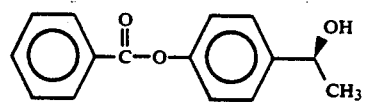

Part B—Preparation of (S)-4-(1-hydroxyethyl)phenyl. Using the procedure described in EXAMPLE 1, Part C, and using (S)-4-(1-hydroxyethyl)phenyl benzoate in lieu of (R)-4-(1-hydroxyethyl)phenyl benzoate, an enantiomer having $[\alpha]_D^{25} = 52.6°$ (c=10, THF) with the following structure, confirmed by NMR spectral analysis, was prepared

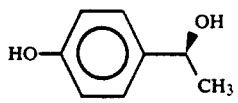

Part C—Preparation of (S)-4-(1-hydroxyethyl)phenyl 4-[2-(2-butoxyethoxy)ethoxyl-biphenyl-4'-carboxylate. Using the procedure described in EXAMPLE 1, Part F, and using (S)-4-(1-hydroxyethyl)phenol in lieu of (R)-4-(1-hydroxyethyl)phenol, an enantiomer having the following structure, confirmed by NMR analysis, was prepared:

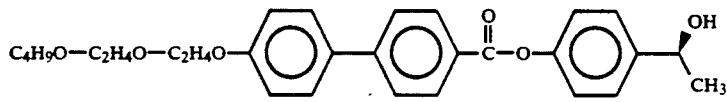

Part D—Preparation of (S)-4-(1-propionyloxyethyl)phenyl 4-[2-(2-butoxyethoxy)ethoxyl-biphenyl-4'-carboxylate. The procedure is described in EXAMPLE 1, Part G, except that: (S)-4-(1-hydroxyethyl)phenyl 4-[2-(2-butoxyethoxy)ethoxy]biphenyl-4'-carboxylate was used in lieu of the (R)-isomer; only 1.1 eq. of triethylamine was used; and 0.2 eq. of 4-dimethylaminopyridine was used as a catalyst. The reactant solution was not cooled in an ice-water bath prior to addition of the propionyl chloride. The product was purified on a flash chromatography column using methylene chloride to yield 40.9 mg (28%) of the desired ester having the following structure as confirmed by NMR spectral analysis.

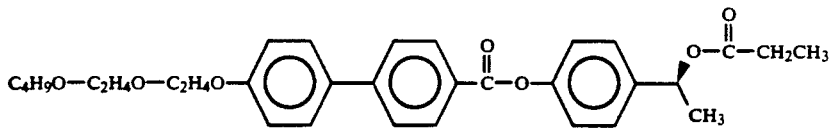

Phase transition temperatures were determined for the compound of this Example, using DSC technique, with the following results:

$$I \xrightarrow[-1.288 \text{ J/g}]{62°} S_A \xrightarrow[-0.343 \text{ J/g}]{51°} S_C \xrightarrow[-13.4 \text{ J/g}]{30°} K$$

$$K \xrightarrow[14.323 \text{ J/g}]{40°} S_C \xrightarrow[0.434 \text{ J/g}]{57°} S_A \xrightarrow[1.47 \text{ J/g}]{69°} I$$

EXAMPLE 3

This example illustrates the preparation of (S)-4-(1-heptanoyloxyethyl)phenyl 4-[2-(2-butoxyethoxy)ethoxy]biphenyl-4'-carboxylate.

The above-named ester compound was prepared using the procedures described in Part D of EXAMPLE 2, except that: heptanoyl chloride was used in lieu of the propionyl chloride; and the starting materials were dissolved in a two-fold volume of methylene chloride. The product was purified on a flash chromatography column using 1:1 pentane/methylene chloride to yield 372.9 mg (60%) of the desired ester having the following structure as confirmed by NMR and mass spectral analyses.

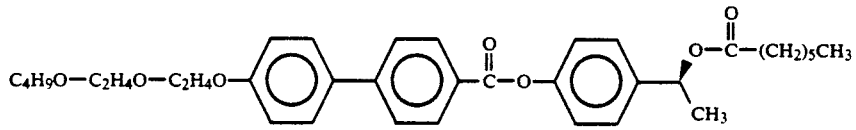

The following phase transition temperatures were recorded, using DSC technique:

$$I \xrightarrow[-7.66 \text{ J/g}]{59°} S_A \xrightarrow{49°} S_C \xrightarrow[-20.6 \text{ J/g}]{32°} K$$

$$K \xrightarrow[43.4 \text{ J/g}]{62°} I$$

EXAMPLE 4

This example illustrates the preparation of (R)-4-(1-heptanoyloxyethyl)phenyl 4-[2-(2-butoxyethoxy)ethoxy]biphenyl-4'-carboxylate.

The above-named compound was prepared using the procedures described in EXAMPLE 3, except that : the (R)-enantiomer of the 4-(1-hydroxyethyl)phenyl 4-[2-(2-butoxyethoxy)ethoxy]biphenyl-4'-carboxylate was used in lieu of the (S)-enantiomer; and also, the only base was 2 eq. of 4-dimethylaminopyridine in lieu of the 4-dimethylaminopyridine/triethylamine mixture. The product was purified on a preparative chromatography plate using 5% ethyl ether/methylene chloride as eluant to yield 98.5 mg (80%) of the desired ester having the following structure as confirmed by NMR spectral analysis.

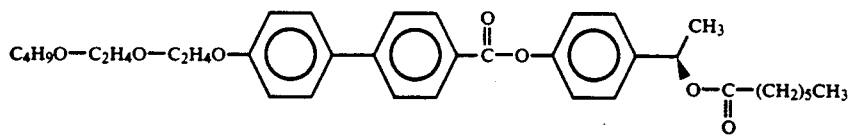

The following phase transition temperature determinations were recorded, using microscopic and DSC techniques.

Microscopy data:

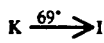

DSC data:

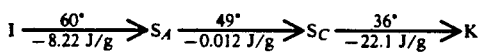

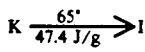

EXAMPLE 5

This example illustrates the preparation of (R)-4-(1-octanoyloxyethyl)phenyl 4-[2-(2-butoxyethoxy)ethoxy]biphenyl-4'-carboxylate.

The above-named ester compound was prepared using the procedure described in Part G of EXAMPLE 1, except that: octanoyl chloride was used in lieu of propionyl chloride; and only 1.1 eq. of triethylamine were used, in lieu of 1.3 equivalents. The product was purified on a preparative chromatography plate using 4% ethyl ether/methylene chloride solution as eluant to yield 64.1 mg (51%) of the desired ester having the following structure as confirmed by $^1$H and $^{13}$C NMR and mass spectral analyses.

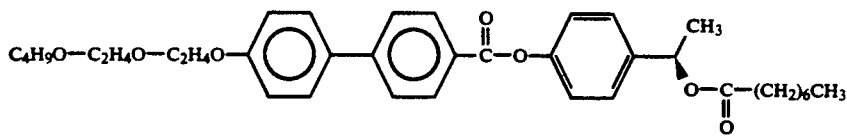

The temperatures of phase transition were obtained using microscopic and DSC techniques and are reported as follows:

Microscopy data:

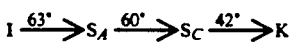

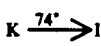

DSC data:

-continued

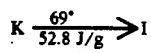

EXAMPLE 6

This example illustrates the preparation of (R)-4-(1-dodecanoyloxyethyl)phenyl 4-[2-(2-butoxyethoxy)ethoxy]biphenyl-4'-carboxylate.

The above-named ester compound was prepared using the procedures described in EXAMPLE 4, except that, the reaction was worked up after only one hour to yield 117.5 mg (85%) of the desired ester having the following structure, as confirmed by NMR and mass spectral analyses.

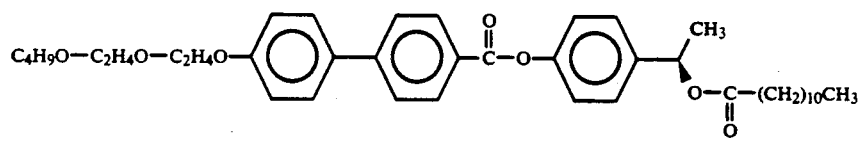

Phase transition temperature, obtained by resort to microscopic and DSC techniques, are reported as follows:

Microscopy data:

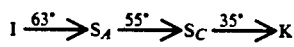

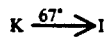

DSC data:

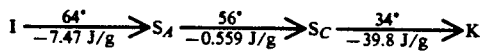

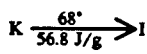

EXAMPLE 7

This example illustrates the preparation of (R)-4-{1-[(S)-2-chloropropionyloxy]ethyl}phenyl 4-[2-(2-butoxyethoxy)ethoxy]biphenyl-4'-carboxylate.

Part A—Preparation of (S)-(−)-2-chloropropionic acid. Two g (17 47 mmol) of L-2-chloropropionic acid sodium salt was dissolved in distilled water. Aqueous hydrochloric acid (10%) was added, with stirring, at room temperature, until the pH of the solution was less than 2. The solution was then extracted with ethyl ether. The organic phase was dried over anhydrous magnesium sulfate and the solvent was removed. The residue was redissolved in methylene chloride, redried over magnesium sulfate, and the solvent was evaporated to yield 1.4 g (74%) of the (S)-(−)-2-chloropropionic acid.

Part B—Preparation of (R)-4-{1-[(S)-2-chloropropionyloxy]ethyl}phenyl 4-[2-(2-butoxyethoxy)ethoxy]-biphenyl-4'-carboxylate. A solution of 200 mg (0.402 mmol) of (R)-4-(1-hydroxyethyl)phenyl 4-[2-(2-butoxyethoxy)ethoxy]biphenyl-4'-carboxylate, prepared as described in Part F of EXAMPLE 1, and 63.4 mg (1.3 eq.) of (S)-(−)-2-chloropropionic acid, 160.2 mg (2 eq.) of EDCI and 25.5 (0.5 eq.) of DMAP in ten ml dry methylene chloride was stirred, under nitrogen, at room temperature overnight. The reaction was quenched with distilled water, and the reaction product was transferred to a separatory funnel, where it was washed with dilute aqueous hydrochloric acid, saturated aqueous sodium bicarbonate solution, and then, twice with water. The organic phase was dried over magnesium sulfate and the solvent was removed. The product was purified on a preparative chromatography plate using 5% ethyl ether/methylene chloride as eluant to yield 142.9 mg (62%) of the desired ester having an optical rotation [α]$_D$= +38.8°, and the following structure, as confirmed by NMR spectral analysis

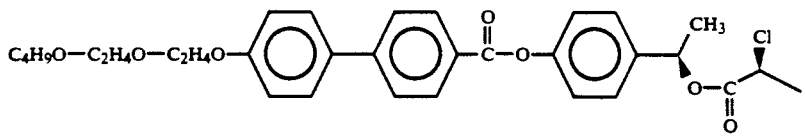

Phase transition temperatures, obtained by microscopic and DSC techniques, are reported as follows:

Microscopy data:

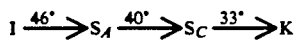

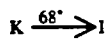

DSC data:

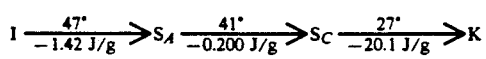

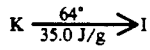

EXAMPLE 8

This example illustrates the preparation of (R)-4-{1-[(R)-2-chloropropionyloxy]ethyl}phenyl 4-[2-(2-butoxyethoxy)ethoxy]biphenyl-4'-carboxylate.

The above-named ester compound was prepared using the procedure described in EXAMPLE 7, except that, (R)-(+)-2-chloropropionic acid was used in lieu of the (S)-enantiomer. Purification on a flash chromatography column using 1% ethyl ether/methylene chloride as eluant yielded 203.9 mg (89%) of the desired ester having the following structure as confirmed by NMR and mass spectral analyses:

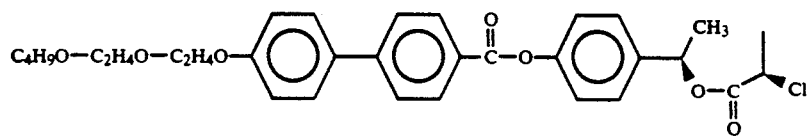

Phase transition temperatures obtained by resort to DSC technique are reported as follows:

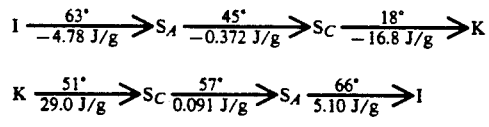

EXAMPLE 9

This example illustrates the preparation of (S)-4-{1-[(S)-2-methylbutyryloxy]ethyl}phenyl 4-[2-(2-butoxyethoxy)ethoxy]biphenyl-4'-carboxylate.

The above-named ester compound was prepared using the procedure described in EXAMPLE 7, except that: the (S)-enantiomer of the 4-(1-hydroxyethyl)phenyl 4-[2-(2-butoxyethoxy)ethoxy]biphenyl-4'-carboxylate was used instead of the (R)-enantiomer; (S)-2-methylbutyric acid was used as the acid; and only 1.5 eq. of EDCI were used. The product was purified on a chromatography column using 10% acetone/methylene chloride solution as eluant to yield 56 mg (100%) of the desired ester having the following formula as confirmed by NMR spectral analysis.

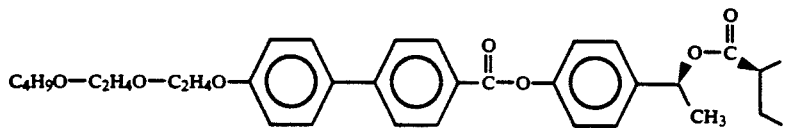

Phase transition temperatures were obtained, using microscopic and DSC techniques and the results are reported as follows:

Microscopy data:

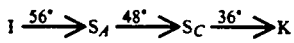

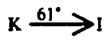

DSC data:

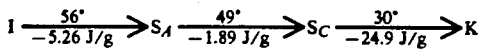

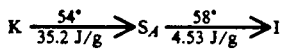

EXAMPLE 10

This example illustrates the preparation of (S)-4-[1-(3-ethoxypropionyloxy)ethyk]phenyl 4-[2-(1H,1H,5H-octafluoro-1-pentoxy)ethoxy]biphenyl-4'-carboxylate.

Part A—Preparation of ethyl 1H, 1H, 5H-octafluoro-1-pentoxy acetate. To 28 g (120 mmol) of 1H, 1H, 5H-octafluoro-1-pentanol in 100 ml of ice cold tetrahydrofuran (THF) were added 2.6 g of sodium hydride (57% oil dispersion). The temperature was kept below 10° C. during addition of the sodium hydride. The mixture was stirred at room temperature for 30 minutes and the solution was used in the following preparation.

The solution was transferred to a separatory funnel and was added to 20.2 g of ethyl bromoacetate in 100 mls of THF at such a rate that the temperature was kept below 5°60 C. After stirring in an ice water-salt bath for one hour, the reaction mixture was stirred at room temperature overnight. Precipitated matter was removed by filtration through diatomaceous earth filtering material (Celite ®) and the THF solution was evaporated in vacuum. The residue was vacuum distilled to give 25.7 g (71%; b.p. 82°-6°/3 mm) of the colorless liquid. the product was the ester having the following structure, confirmed by NMR and mass spectral analyses:

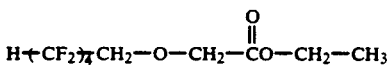

Part B—Preparation of 2-(1H, 1H, 5H-octafluoro-1-pentoxy)ethanol. To a suspension of 2.6 g of lithium aluminum hydride in 200 mls of ether was added a solution of 100 mls of ether and 19.5 g (200 mmol) of the product obtained in the manner described in Part A of this example. The solution was added at such a rate as to maintain a gentle reflux. After stirring at room temperature for 2.5 hours, six mls of water were carefully added in a dropwise manner to destroy excess lithium aluminum hydride. The resulting paste was stirred for 1.5 hours and filtered and the precipitate was thoroughly washed with ether. The ether solutions were combined and dried over anhydrous sodium sulfate. Solvent was removed under reduced pressure. The residue was vacuum distilled to give 15.22 g (86%), b.p,. 74°-77° C./3 mm of colorless liquid product having the following formula, confirmed by NMR and mass spectral analyses:

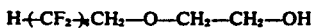

Part C—Preparation of p-tosylate of 2-(1H, 1H, 5H-octafluoro-1-pentoxy)ethanol. To a solution of 6.5 g (23.55 mmol) of product obtained in Part B of this example, in 35 mls of pyridine, were added 8.73 g of p-toluenesulfonyl chloride. The addition was performed at a slow rate so as to maintain the temperature below 5° C. After the addition, the resulting reaction mixture was stirred in an ice-methanol bath for one hour and was kept in a refrigerator overnight. The reaction mixture was poured into 300 mls of ice water and the aqueous solution was extracted twice with methylene chloride (125 mls each extraction). The methylene chloride solutions were combined and washed twice with 100 mls of 5% aqueous hydrochloric acid and three times with 100 mls of water. The methylene chloride solution was dried over anhydrous sodium sulfate and evaporated to give 9.5 g of an orange oil residue. The oil was passed through a silica gel chromatographic column (50 g of 60–200 mesh silica gel) using 1:1 hexane/methylene chloride eluant. An amount of 8.7 g (86%) of a pale-yellow oil was obtained having the following formula confirmed by NMR and mass spectral analyses:

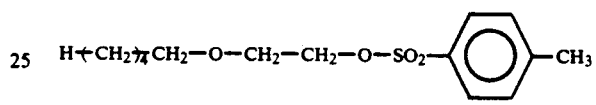

Part D—Preparation of methyl 4-[2-(1H, 1H, 5H-octafluoro-1-pentoxy)ethoxylbiphenyl-4'-carboxylate A mixture of 4.3 g of the product of Part C of this example, and 2.3 g of methyl 4-hydroxy-4'-biphenyl carboxylate, and pulverized anhydrous potassium carbonate (2.8 g) in 40 mls of dimethylformamide was heated for four hours at 125°-130° C. The reaction mixture was poured into 400 mls of ice water and was filtered to give 4.6 g of a crude product. The product was dissolved in ethyl ether and the ether solution was washed with water, dried over anhydrous sodium sulfate and evaporated to give a yellowish solid. The product was triturated with 50 mls of hexane for two hours, yielding 3.65 g of a colorless solid having a melting point of 120°-123° C. An additional 0.12 g of product was recovered by cooling the filtrate in a freezer overnight. Overall yield was 80%. The product was the methyl ester having the following formula, confirmed by NMR and mass spectral analyses

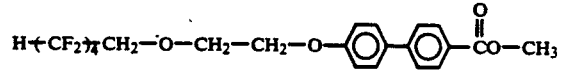

Part E—Preparation of 4-[2-(1H, 1H, 5H-octafluoro-1-pentoxy)ethoxylbiphenyl-4'-carboxylic acid. Three grams of the methyl ester of Part D of this example were dissolved into 100 mls of methanol, 5 mls of 45% aqueous potassium hydroxide solution and 100 mls of water. The solution was heated on a steam bath until all the methanol was removed by evaporation. The homogeneous aqueous solution was acidified with concentrated hydrochloric acid to a pH of about 1, was cooled in an ice water bath and filtered. The precipitate was dried at 60° C. in a vacuum oven overnight, yielding 2.82 g (97%) of a colorless solid, m.p. 149°-152° C. The product was the acid having the following formula, confirmed by NMR and mass spectral analyses.

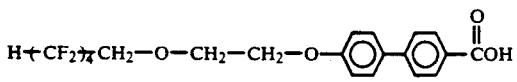

Part F—Preparation of (S)-4-(1-hydroxyethyl)phenyl 4-[2-(1H, 1H, 5H-octafluoro-1-pentoxy)ethoxy]biphenyl-4'-carboxylate. Using the procedure described in Part C of EXAMPLE 2, and using the 4-[2-(1H, 1H, 5H-octafluoro-1-pentoxy)ethoxy]biphenyl-4'-carboxylic acid of Part E of this example in place of the 4-[2-(2-butoxyethoxy)ethoxy]biphenyl-4'-carboxylic acid, the desired ester of the following structure, as confirmed by NMR and mass spectral analyses, was prepared.

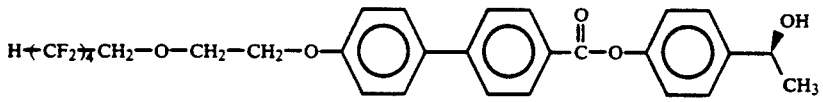

Part G—Preparation of (S)-4-[1-(3-ethoxypropionyloxy)ethyl]phenyl 4-[2-(1H, 1H, 5H-octafluoro-1-pentoxy)ethoxY]biphenyl-4'-carboxylate. The procedure of EXAMPLE 9 was employed except that: one equivalent of 3-ethoxypropionic acid was used in place of (S)-2-methylbutyric acid; 1.3 eq. of 4-dimethylaminopyridine were used; a ten-fold volume of solvent was used; and (S)-4-(1-hydroxyethyl)phenyl 4-[2-(1H, 1H, 5H-octafluoro-1-pentoxy)ethoxy]biphenyl-4'-carboxylate was used in place of the (S)-4-(1-hydroxyethyl)phenyl 4-[2(2-butoxyethoxy)ethoxy]biphenyl-4'-carboxylate.

Purification by flash chromatography with 0.5% methanol in methylene chloride/hexanes as eluant yielded 91mg (52%) of the desired ester of the following structure, as confirmed by NMR spectral analysis:

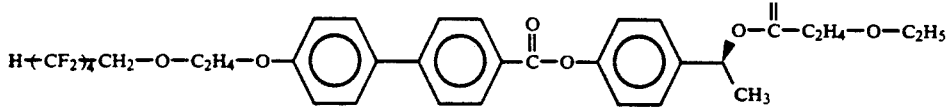

Phase transition temperatures, obtained by resort to microscopic and DSC techniques, are reported as follows:

Microscopy data:

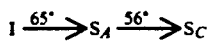

DSC data:

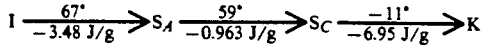

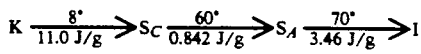

EXAMPLE 11

This example illustrates the preparation of (R)-4-(1-octanoyloxyethyl)phenyl 4-[2-(1H, 1H, 5H-octafluoro-1-pentoxy)ethoxy]biphenyl-4'-carboxylate.

Part A—Preparation of (R)-4-(1-hydroxyethyl)phenyl 4-[2-(1H, 1H, 5H-octafluoro-1-pentoxy)ethoxy]biphenyl-4'-carboxylate. The procedure described in Part F of EXAMPLE 1 was employed, except that: 4-[2-(1H, 1H, 5H-octafluoro-1-pentoxy)ethoxy]biphenyl-4'-carboxylic acid was used in lieu of 4-[2-(2-butoxyethoxy)ethoxy]biphenyl-4'-carboxylic acid; and purification was effected by preparative thin layer chromatography with 10% ethyl ether/methylene chloride instead of by flash chromatography. The desired ester of the following structure, as confirmed by NMR analysis, was prepared:

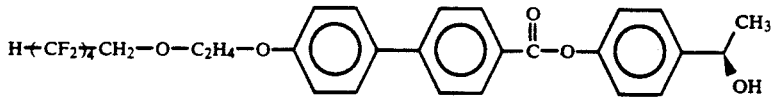

Part B—Preparation of (R)-4-(1-octanoyloxyethyl)phenyl 4-[2-(1H, 1H, 5H-octafluoro-1-pentoxy)ethoxy]biphenyl-4'-carboxylate. The procedure described in EXAMPLE 4 was employed, except that: (R)-4-(1-hydroxyethyl)phenyl 4-[2-(1H, 1H, 5H-octafluoro-1-pentoxy)ethoxy]biphenyl-4'-carboxylate was used in lieu of (R)-4-(1-hydroxyethyl)phenyl 4-[2-(2-butoxyethoxy)ethoxy]biphenyl-4'-carboxylate; and purification was effected by preparative thin layer chromatography with 30% hexanes/methylene chloride. The desired ester of the following structure, as confirmed by NMR analysis, was prepared:

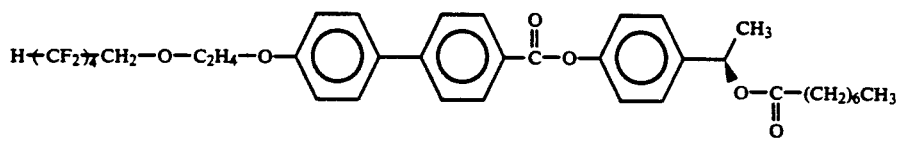

Phase transition temperatures, obtained by resort to microscopic and DSC techniques, are reported as follows:

Microscopy data:

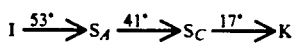

DSC data:

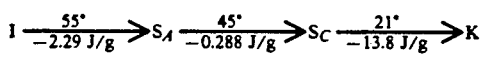

EXAMPLE 12

Compounds of the invention were evaluated for determination of spontaneous polarization. Measurements, where obtained, were obtained using a ferroelectric cell containing the test compound. The ferroelectric cell was formed by scribing a pair of lines onto one of a pair of indium tin oxide-coated glass substrates; spin coating each of the electrode glass plate elements with a layer of Nylon 66 polyamide; rubbing each of the polyamide layers; pairing the electrode plate elements (spaced apart about 2.4 to 5 microns by a peripheral edge spacer, with the rubbed orientations being in parallel); and filling the cell with the sample liquid crystal material Measurement of charge, over the known area defined by the scribed lines, was performed using a capacitive bridge circuit according to known technique. Measurement of spontaneous polarization was, in each instance, conducted at a temperature within the range of temperatures showing smectic behavior, as reported hereinbefore for each of the compounds. Spontaneous polarization ($P_S$) values are expressed in nanocoulombs per square centimeter ($nC/cm^2$); and the temperatures at which the $P_S$ values were obtained are reported along with such values in Table 1, as follows:

TABLE 1

| Compound of EXAMPLE | Spontaneous Polarization ($nC/cm^2$) | Temperature (°C.) |
|---|---|---|
| 1 | +225 | 32 |
| 2 | — | — |
| 3 | −240 | 40 |
| 4 | +248 | 40 |
| 5 | +260 | 40 |
| 6 | +137 | 41 |
| 7 | +110 | 33 |
| 8 | +112 | 28 |
| 9 | −210 | 35 |
| 10 | −198 | 25 |
|  | −205 | 20 |
| 11 | +285 | 27 |

What is claimed is:

1. A liquid crystal compound having the formula

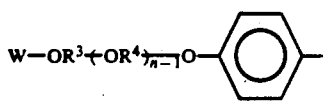

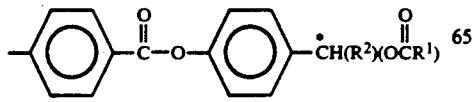

wherein $R^1$ is alkyl of from 1 to 16 carbon atoms; alkoxy of from 1 to 6 carbon atoms; haloalkyl of from 1 to 3 carbon atoms and from 1 to 3 halogen atoms; alkyl in which from one to three non-adjacent methylene groups may be replaced by an oxygen ether atom; in which from one to three non-adjacent methylene groups may be replaced by an oxygen ether atom; $R^2$ is alkyl of from 1 to 4 carbon atoms; each of $R^3$ and $R^4$ is alkylene having from 1 to 6 carbon atoms; n is an integer 1 or 2; and W is alkyl of from 1 to 12 carbon atoms or fluoroalkyl of the formula

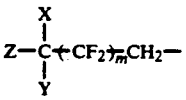

wherein each of X, Y and Z is hydrogen or fluorine, m is zero or an integer from 1 to 6, and at least one of X, Y and Z is fluorine when m is zero.

2. The liquid crystal compound of claim 1 wherein $R^1$ is alkyl of from 1 to 16 carbon atoms.

3. The liquid crystal compound of claim 2 wherein W is alkyl of from 1 to 12 carbon atoms.

4. The liquid crystal compound of claim 3 wherein W is alkyl of from 1 to 4 carbon atoms.

5. The liquid crystal compound of claim 4 wherein n is 2.

6. The liquid crystal compound of claim 5 wherein each of $R^3$ and $R^4$ is 1,2-ethylene.

7. The liquid crystal compound of claim 6 wherein W is n-butyl.

8. The liquid crystal compound of claim 6 wherein $R^2$ is methyl.

9. The liquid crystal compound of claim 6 wherein $R^1$ is ethyl.

10. The liquid crystal compound of claim 6 wherein $R^1$ is n-hexyl.

11. The liquid crystal compound of claim 6 wherein $R^1$ is n-heptyl.

12. The liquid crystal compound of claim 6 wherein $R^1$ is n-undecyl.

13. The liquid crystal compound of claim 6 wherein $R^1$ is 2-butyl.

14. The liquid crystal compound of claim 6 wherein $R^1$ is haloakyl of from one to three carbon atoms and one to three halogen atoms.

15. The liquid crystal compound of claim 14 wherein said haloalkyl is 1-chloroethyl.

16. The liquid crystal compound of claim 4 wherein n is 1 and $R^3$ is 1,2-ethylene.

17. The liquid crystal compound of claim 1 wherein W, is alkyl of from 1 to 4 carbon atoms.

18. The liquid crystal compound of claim 17 wherein n is 1 and $R^3$ is 1,2-ethylene.

19. The liquid crystal compound of claim 18 wherein $R^2$ is methyl.

20. The liquid crystal compound of claim 19 wherein $R^1$ is alkyl of from 1 to 16 carbon atoms.

21. The liquid crystal compound of claim 1 wherein W is fluoroalkyl of the formula

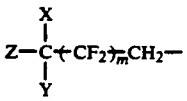

wherein each of X, Y and Z is hydrogen or fluorine and m is zero or an integer from 1 to 6.

22. The liquid crystal compound of claim 21 where Z is hydrogen and each of X and Y is fluoro.

23. The liquid crystal compound of claim 22 wherein m is an integer from 1 to 5.

24. The liquid crystal compound of claim 23 wherein m is 3.

25. The liquid crystal compound of claim 24 wherein $R^2$ is methyl.

26. The liquid crystal compound of claim 25 wherein $R^1$ is n-heptyl.

27. The liquid crystal compound of claim 25 wherein $R^1$ is alkyl comprising a chain of carbon atoms including one oxygen ether atom.

28. The liquid crystal compound of claim 25 wherein $R^1$ is ethoxyethyl.

* * * * *